US006479438B2

(12) United States Patent
Narayanan et al.

(10) Patent No.: US 6,479,438 B2
(45) Date of Patent: Nov. 12, 2002

(54) GEL INHIBITED LIQUID CARRIER FOR A BIOCIDE CONTAINING A CARBODIIMIDE AND AN EMULSIFIER MIXTURE

(75) Inventors: Kolazi S. Narayanan, Wayne, NJ (US); Domingo I. Jon, New York, NY (US)

(73) Assignee: ISP Investments Inc., Wilmington, DE (US)

( * ) Notice: Subject to any disclaimer, the term of this patent is extended or adjusted under 35 U.S.C. 154(b) by 18 days.

(21) Appl. No.: 09/754,172

(22) Filed: Jan. 4, 2001

(65) Prior Publication Data

US 2002/0128153 A1 Sep. 12, 2002

(51) Int. Cl.[7] .................. A01N 25/04; A01N 25/22; A01N 37/52; A01N 43/68; A01N 47/36
(52) U.S. Cl. .................. 504/363; 514/254; 514/637; 514/788
(58) Field of Search .................. 504/211, 363; 514/788, 254, 637

(56) References Cited

U.S. PATENT DOCUMENTS

| 4,812,466 | A | * | 3/1989 | Boger et al. ............... 514/351 |
| 5,045,536 | A | * | 9/1991 | Baker ......................... 514/63 |
| 5,731,264 | A | * | 3/1998 | Narayanan et al. ......... 504/116 |
| 6,255,350 | B1 | * | 7/2001 | Jon et al. .................... 514/588 |

* cited by examiner

Primary Examiner—S. Mark Clardy
(74) Attorney, Agent, or Firm—Marilyn J. Maue; William J. Davis; Walter Katz

(57) ABSTRACT

This invention relates to a biocidal composition resistant to the formation of a gel and to the method for stabilizing a concentrate containing, in addition to the biocide, a carbodiimide in monomeric or polymeric form or a mixture thereof and a lipophilic/hydrophilic emulsifier mixture having a HLB of at least 7 comprising an oil and an alkoxylated ester of a polyhydroxylated compound, by adding to the concentrate between about 0.5 and about 15 wt. % of a saturated, aliphatic compound having a molecular weight of less than 400, selected from the group consisting of a polyhydroxyated alkanol and/or a polyhydroxylated ketone.

21 Claims, No Drawings

GEL INHIBITED LIQUID CARRIER FOR A BIOCIDE CONTAINING A CARBODIIMIDE AND AN EMULSIFIER MIXTURE

BACKGROUND OF THE INVENTION

Liquid carrier compositions for herbicides, insecticides, fungicides and other biocidally active compounds which contain an emulsifier mixture of an oil and an alkoxylated ester of a polyhydroxylated hydrocarbon and a carbodiimide or polymer thereof are useful agrochemical solutions and additionally have several other non-agrochemical uses including diluents for forming oil-in-water (O/W) or water-in-oil (W/O) microemulsions for cleaning and disinfecting formulations, pesticidal sprays or dips for treating livestock and domesticated pets, etc. The concentrates also find use as additives to existing commercial formulations for the stabilization many active compounds. Such concentrates are particularly useful for preventing or minimizing the degradation of water soluble biocidally active aza compounds. Typically, a formulation containing aza compounds in a concentrate is disclosed in our co-pending co-pending U.S. patent application, Ser. No. 09/169,697. This anhydrous concentrate additionally contains a carbodiimide, a $C_{8-18}$ alkyl lactam and a lipophilic/hydrophilic emulsifier mixture. The compositions disclosed in this patent are suitably employed for the present treatment preventing gel formation and are incorporated herein by reference.

While several prior concentrate carriers containing a carbodiimide and an emulsifier mixture are highly effective in producing microemulsions and initially sprayable liquids which are stabilized against decomposition of the active agent, it has been found that in many cases the active carrier itself is subject to gel formation during subsequent handling or storage, particularly during storage at elevated temperatures, or when higher concentrations of the alkoxylated esters or carbodiimide, water scavenging agent, are present in the concentrate. Since, for certain applications including pump and aerosol sprays, crop spraying and animal dips, gel formation is undesirable, extensive research has been directed to extending the shelf life of such concentrates or solutions to accommodate delayed use of at least a portion of the liquid concentrate.

Accordingly it is an object of this invention to overcome the above problem by providing a diluent solution or concentrate which does not undergo thickening or gelling for a period up to 6 months or more while retaining stability of the active component and other desirable formulation characteristics.

Another object is to provide a pesticidal microemulsion suitable for spray or dip administration to crops, livestock and pets.

Another object is to provide an effective and economical gel inhibited formulation containing a stabilized biocidally active compound in aqueous solution which has extended shelf life at both ambient and elevated temperatures.

These and other objects of the invention will become apparent from the following description and disclosure.

SUMMARY OF THE INVENTION

In accordance with this invention there is provided a stable anhydrous, gel free, liquid concentrate having a Brookfield viscosity less than 1,000 cps essentially containing, as the concentrate, (i) an active biocidal component, (ii) a carbodiimide and (iii) a lipophilic/hydrophilic emulsifier mixture having an HLB of 7–20, to which is added between about 0.5 and about 15 wt. %, based on total concentrate composition, of an anti-gelling agent which is a saturated, aliphatic compound having a molecular weight of less than 400 and selected from the group consisting of a polyhydroxylated alkanol, a polyhydroxylated ketone, a carbohydrate or a mixture thereof. Additionally the concentrate may contain from 0 to 40 wt. % of an oil solvent for certain anti-gelling agents which are not readily assimilated in the concentrate system.

DETAILED DESCRIPTION OF THE INVENTION

The liquid concentrates of this invention comprise formulations containing between about 0.05 and about 25 wt. % of a biocidally active, hydrolytically unstable, component which includes insecticidal, fungicidal, pesticidal and herbicidal compounds which include the class of aza compounds containing the structure —C—N—where one of the free carbon bonds can form a double bond to the nitrogen, such as in an imidine, for example, N-methyl bis(2,4-xylyl iminomnethyl amine) [AMITRAZ], n-cyclopropyl-1,3,5-triazine-2,4,6-triamine [Cyromazine], chlorsulfuron, sulfometuron, metsulfuron-methyl, thifensulfuron and the like, of which AMITRAZ is preferred. The aza compounds are those normally employed to treat livestock, such as sheep or cattle, feral animals and household pets such as dogs, cats and the like. Other suitable aza compounds are those disclosed in my copending U.S. patent application, Ser. No. 09/169,697 and U.S. Pat. No. 5,731,264, incorporated herein by reference.

Instant concentrate may contain between about 5 and about 40 wt. % water soluble or water insoluble organic solvent for water soluble or water insoluble active components. Such organic solvents include ethanol, cyclohexane, N-alkyl lactam, cyclic lactone and $C_8$ to $C_{12}$ alkyl pyrrolidone and mixtures thereof; N-octyl pyrrolidone being preferred.

The present composition essentially contains between about 2 and about 20 wt. % of a carbodiimide, in monomeric or polymeric form, having water scavenging and dehydrating functionality. Preferably, the carbodiimide is incorporated at a concentration of between about 5 and about 15 wt. %. Suitable carbodiimide scavenging agents are terminally hindered carbodiimides having a polymeric or non-polymeric substituent on a terminal imide nitrogen. The terminal substituent is a non-functional linear, branched, cycloaliphatic, heterocyclic or an aromatic radical and can be defined by the following formulae A and B

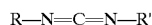

R—N=C=N—R'   A.

wherein R and R' are each individually aliphatic, aromatic, alkylaromatic carbocyclic or heterocyclic radicals. At least one of R and R' is most desirably a hindered alkyl substituted phenyl group, such as the 2,6-diisopropyl phenyl group and

—[N=C=N—X]$_n$—   B.

wherein n has a positive value up to 100; preferably a value of 10–20, and X is an alkyl substituted phenylene group, for example 2,4,6-tri isopropyl phenyl. Of these, the carbodiimides having a terminal nitrogen atom substituted with alkylphenyl, alkoxyalkylphenyl, sulfonate, sulfonamide, imido, imidoester, and sulfonyl urea groups are most effective. Particularly preferred scavengers are bis(tetra-isopropyl phenyl)carbodiimide, bis(hydroxyphenyl) carbodiimide and bis(di-isopropylphenyl carbodiimide, e.g. (STABAXOL I) supplied by Rhein Chemie).

The carbodiimide component in the concentrate is polyfunctional in that it acts not only as a waterscavenger but also becomes part of a micelle which envelops water insoluble biocides so that, upon subsequent dilution of the concentrate with water, a homogeneous liquid emulsion, suitable for spray application, can be obtained. While the water scavenging function of the carbodiimide can be replaced, in whole or in part, by a less costly inorganic water scavenger, e.g. an inorganic oxide, or other organic water scavenger sufficient carbodiimide must be retained in the concentrate to assure micellar containment of the water insoluble active component in the subsequent formation of a homogeneous emulsion suitable for plant spraying or immersion or spraying of animals. Further the carbodiimide which is present in the micellar composition protects the enveloped active component from water thus preventing hydrolytic decomposition.

The emulsifier portion of the present liquid composition comprises between about 25 and about 85 wt. %, preferably between about 40 and 60 wt. %, of the composition and is a mixture of lipophilic and hydrophilic surfactants having a HLB of from 7 to 20, preferably 9–11.

In general, the lipophilic character of the present emulsifiers is enhanced by a lower number of alkoxy groups in the compound or the higher molecular weight of an alkyl group in the N-alkyl lactam or ester; whereas hydrophilic character of the emulsifier is enhanced by a higher number of alkoxy groups, e.g. >30, or lower alkyl lactams or esters. Thus, if desired the lipophilic/hydrophilic emulsifier mixture can contain mixtures of the same oil with varying degrees of alkoxy substitution, mixtures of lower and higher alkyl lactams, etc. Preferably, the lipophilic/hydrophilic mixture contains emulsifiers which may have from 8 to 60 $C_2$ to $C_3$ alkoxy groups and the preferred mixture has an acid number of <5.

Representative examples of suitable lipophilic emulsifiers include alkoxylated mineral oils, vegetable oils, triglycerides such as castor oil, soybean oil, linseed oil, rapeseed oil, $C_6$ to $C_{18}$ alkyl lactams and mixtures thereof. Suitable lipophilic oils are those having from 2 to 30 units of $C_2$ to $C_3$ alkoxy units. Of these, ethoxylated castor oils containing 12–40 ethoxy units, available as ALKAMULS® EL or CO 15, supplied by Rhone Poulenc, are preferred.

Representative examples of the hydrophilic emulsifiers include hydroxylated, alkoxylated esters derived from condensates of carboxylic acids such as sorbic-, oleic-, stearic- and palmitic-acids and generally contain 10 to 80, more desirably 15 to 60, alkylene groups. These hydrophilic esters also contain from 8 to 60 alkoxy units as in alkoxylated sorbitan monooleate and alkoxylated castor oil. Other hydrophilic emulsifiers, such as anionic alkyl phosphates and sulfonates can also be used as well as alkoxylated reduced sugars, e.g. saturated alkoxylated sorbitan, etc. Mixtures of these or optionally at least one of these in combinations with the above acid condensate esters may form the hydrophilic portion of the emulsifier mixture. To obtain a desirable HLB, between about 20 and about 80 wt. % of an alkoxylated lipophilic oil and between about 80 and about 20 wt. % of a hydrophilic hydroxylated, alkoxylated ester is recommended. Of the hydrophilic emulsifiers ethoxylated sorbitan mono-, di- and/or tri-oleate, e.g. (ALKAMULS® PSMO 20, Rhone Poulenc) and $C_8$ to $C_{12}$ alkyl phosphates are preferred.

The above concentrate composition optionally contains 0 up to 40 wt. % of a diluent oil in addition to any oil employed for the lipophilic/hydrophilic emulsion mixture. The oil additive is employed as a solvent for certain highly branched poly hydroxy anti-gelling agents, e.g. pentaerythritol, glycerol, sorbitol, or other components of the concentrate composition, and also can be used to regulate the concentration of the active in the concentrate composition, when such control is desired. Suitable organic oil supplements include, non-alkoxylated vegetable oils, petroleum distillates, hydrocarbon solvents and the like.

The liquid concentrate compositions can also contain additional additives and inert excipients to satisfy the needs of the consumer or the requirements of a certain active component in emulsion or solution. The aza pesticidal concentrate compositions disclosed in co-pending U.S. patent application, Ser. No. 09/169,697 and U.S. Pat. No. 5,731,264 are most suitably employed in the present invention involving the anti-gelling additive.

The present dip and spray concentrate/anti-gellant formulations at the above described concentrations are inhibited against gel formation during storage at both ambient and elevated temperatures by the addition of the present polyhydroxylated alkanol and/or polyhydroxylated ketones. The above liquid concentrates or solutions of this invention contain between about 0.5 and about 15 wt. %, preferably between about 1 and about 10 wt. %, based on the total concentrate or solution composition, of an aliphatic polyhydroxylated anti-gelling agent. Suitable anti-gelling agents are saturated organic compounds having a molecular weight less than 400 and are selected from the group of polyhydroxylated alkanols and/or polyhydroxylated ketones containing from 2 to 10 hydroxy groups or carbohydrate groups, preferably in reduced form, as in sorbitol. The $C_2$ to $C_6$ hydroxylated alkanols and/or ketones are preferred. Representative examples of such anti-gelling agents include ethylene glycol, propylene glycol, 1,4-butanediol, pentaerythritol, glycerol, glyceraldehyde, dihydroxyacetone, 1,4-dihydroxyacetone dimer, 1,3-dihydroxyacetone dimer, trihydroxyacetone, sorbitol, cyclohexane diol, inositol, 2,4,6-trihydroxy cyclohexanone, 4,4'-dihydroxy cyclohexyl ketone and the like. Anti-gellant concentrations of between about 1 and about 6 wt. %, based on total concentrate composition, are most preferred.

The present composition can be prepared by simply contacting the above mixture of concentrate components and the anti-gelling agent, under agitation at ambient temperature up to about 70° C. until a homogeneous composition is obtained. Alternatively, the concentrate components can be premixed and the anti-gelling agent added subsequently.

Having generally described the invention, reference is now had to the following examples which set forth comparisons and preferred embodiments but which are not to be construed as limiting to the scope of the invention as defined in the appended claims.

EXAMPLE 1

The following carrier composition (95 g) for bioactive compounds, such as e.g., AMITRAZ, was prepared by mixing the ingredients shown in following Table A. The ingredients of the composition were combined in the amounts indicated and were mixed for 24 hours at room temperature in a one ounce glass stoppered bottle mounted on a rotary wheel.

A half portion of the above composition was then stored t room temperature and within 10 days formed an unsprayable gel. The second half portion of the above composition, which was stored in an oven maintained at 50° C., gelled in 24 hours.

TABLE A

| Ingredient | weight in grams |
|---|---|
| N-octyl pyrrolidone (Agsol EX 8) | 20.0 |
| Ethoxylated castor oil (15 EO), ALKAMULS CO-15 | 36.0 |
| Ethoxylated Sorbitan monooleate (20 EO), TWEEN 80 | 30.0 |
| Tetra isopropyl biphenyl carbodiimide, STABAXOL I | 9.0 |
| Total | 95.0 |

EXAMPLES 2 THROUGH 9

To each of eight 9.5 g samples of the carrier composition, prepared as described in Example 1, was added 0.5 g of the hydroxylated alcohol or ketone reported in following Table B. The 0.5 g additive was omitted from one of the 9.5 g samples which was reserved as a control. Each of the above compositions were individually recovered and stored at 50° C. and the minimum days required for gel formation was recorded and reported in Table B.

TABLE B

| Example | Additive (5 wt. %) | Min. Days for Gel Formation |
|---|---|---|
| 2 | none (control sample) | 1 |
| 3 | 1,3-dihydroxy acetone dimer | >26 |
| 4 | 1,2,3-trihydroxy propane (glycerol) | 16 |
| 5 | sorbitol as 70% aqueous solution | >26 |
| 6 | 2-methoxy ethanol | 5 |
| 7 | 2-methyl isopropanol | 5 |
| 8 | methanol | 7 |
| 9 | sorbitol/glycerol (25:75) | >26 |

EXAMPLE 10

A concentrate was prepared at room temperature by mixing 5 g. of AMITRAZ in 18.7 g of N-octylpyrrolidone, 33.6 g. of 16 (EO) ethoxylated castor oil, 28 g. of 20 (EO) ethoxylated sorbitan monooleate, 8.6 g of STABAXOL I, 4.75 g. of glycerol and 1.33 g. of D-sorbitol. After storage for 69 days at 50° C. the product remained free of gel.

Example 10 is repeated except that Cyromazine is substituted for AMITRAZ. The resulting product remains gel free after storage at 50° C. for at least 15 days.

The same result is obtained when chlorsulfuron is substituted for AMITRAZ.

EXAMPLE 11

A concentrate was prepared at room temperature by mixing 5 g. of ARMITRAZ in 15 g. of N-octylpyrrolidone, 10 g. of isopropyl alcohol, 30 g. of 15 (EO) ethoxylated castor oil, 28 g. of 20 (EO) ethoxylated sorbitan monooleate, 10 g. of STABAXOL I and 2 g. of pentaerythritol anti-gellant. After storage for 10 days at 50° C., the product remained gel free.

EXAMPLE 12

A concentrate was prepared at room temperature by mixing 5 g. of AMITRAZ in 15 g. of N-octylpyrrolidone, 34 g. of 15(EO) ethoxylated castor oil, 30 g. of 20(EO) ethoxylated sorbitan monooleate, 10 g. of STABAXOL I and 6 g. of 1,4-butanediol. After storage for 10 days at 50° C., the product remained gel free.

It will be understood that many modifications and substitutions can be made in the above examples to achieve the present anti-gelling concentrates without departing from the scope of this invention. For example, other aza biocides disclosed herein can be substituted for AMITRAZ as well as other substitutions in the emulsifier mixture to achieve an HLB of 7–20, preferably 7–11.

What is claimed is:

1. A gel resistant, biocidally active concentrate or solution containing (a) between about 0.05 and about 25 wt. % a biodially active component; (b) between about 0 and about 40 wt. % of an organic oil; (c) between about 2 and about 20 wt. % of a terminally hindered carbodiimide; (d) between about 10 and about 80 wt. % of a lipophillic/hydrophilic emulsifier mixture having HLB of from about 7 to 20 and (e) between 0.5 and about 15 wt. %, based on (a)through (d), of a polyhydroxylated, aliphatic compound selectyed from the group consisting of propylene glycol, 1,4-botanediol, pentaerythritol, glycerol, glyceraldehydes, dihydroxyacetone, 1,4-dihydroxyacetone dimmer, 1,3-dihydroxyacetone dimmer, trihydroxy acetone, sorbitol, cyclohexane diol, inositol, 2,4,6-trihydorxy cyclohexanoe, 4,4'-dihydroxy cyclohexyl ketone and a mixture therof; said polyhydroxylated compound having a molecular weight less than 400.

2. The composition of claim 1 wherein said carbodiimide contains a terminal nitrogen atom substituted with a radical selected from the group consisting of a lower alkyl phenyl, sulfonate, sulfonamide, imido, imidoester.

3. The composition of claim 2 wherein said carbodiimide is bis(tetra- and/or di-isopropyl phenyl)carbodiimide.

4. The composition of claim 2 wherein said carbodiimide is bis(hydroxyphenyl)carbodiimide.

5. The composition of claim 1 wherein said emulsifier mixture has an acid number greater than 5.

6. The composition of claim 5 wherein said emulsifier mixture includes an oil containing 5 to 60 $C_2$ to $C_3$ alkoxy groups.

7. The composition of one of claims 1 or 6 wherein said emulsifier mixture includes an ethoxylated castor oil.

8. The composition of one of claims 1 or 6 wherein said hydrophilic emulsifier is a hydroxylated ester of a carboxylic acid which contains 5 to 60 $C_2$ to $C_3$ alkoxy units or a mixture thereof.

9. The composition of one of claims 1 or 6 wherein said hydrophilic emulsifier is selected from the group consisting of an ethoxylated sorbitan mono-, di- and/or tri-oleate and a $C_8$ to $C_{12}$ alkyl phosphate or a mixture thereof.

10. The composition of claim 1 wherein said polyhydroxylated compound is employed at a concentration of between about 1 and about 10 wt. % of components (a) through (d) of the concentrate composition.

11. The composition of one of claims 1 or 10 wherein said polyhydroxylated compound contains from 2 to 6 hydroxy groups and is selected from the group consisting of 1,4-butanediol, pentaerithritol, glylcerol, dihydroxyacetone, 1,4-dihydroxyacetone dimer, 1,3-dihydorxyacetone dimer, trihydroxyacetone and sorbitol.

12. The composition of claim 1 wherein said polyhydroxylated compound is sorbitol.

13. The composition of claim 1 wherein said polyhydorxylated compound is glycerol.

14. The composition of claim 1 wherein said polyhydorxylated compound is 1,3-dihydroxy acetone dimer.

15. The composition of claim 1 wherein the HLB of the emulsifier mixture is between 7 and 11.

16. The composition of claim 10 wherein the concentration of the anti-gelling agent is between about 3 and about 10 wt. % of components (a) through (d) of the concentrate composition.

17. A homogeneous miniemulsion comprising the concentrate and anti-gelling agent of claim 1 diluted with solvent to between about 1:10 and about 1:10,000 parts of concentrate to parts of olvent.

18. The miniemulsion of claim 17 wherein the solvent is water and the active component is a water soluble or water insoluble compound.

19. The miniemulsion of claim 17 wherein the active component is water insoluble.

20. The miniemulsion of claim 17 wherein the active compound is N-cyclopropyl-1,3,5-triazine-2,4,6-triamine or N-methyl bis(2,4-xylyliminomethyl amine).

21. The concentrate of claim 17 which is diluted between about 1:10 and about 1:1,000 with water.

* * * * *